(12) United States Patent
Karpen (10) Patent No.: US 8,217,646 B2
(45) Date of Patent: Jul. 10, 2012

(54) INSPECTION APPARATUS FOR PERFORMING INSPECTIONS

(75) Inventor: Thomas Karpen, Skaneateles, NY (US)

(73) Assignee: GE Inspection Technologies, LP, Lewistown, PA (US)

( * ) Notice: Subject to any disclaimer, the term of this patent is extended or adjusted under 35 U.S.C. 154(b) by 576 days.

(21) Appl. No.: 12/253,548

(22) Filed: Oct. 17, 2008

(65) Prior Publication Data

US 2010/0097057 A1    Apr. 22, 2010

(51) Int. Cl.
*G01N 27/72* (2006.01)

(52) U.S. Cl. .......................... 324/228; 324/219

(58) Field of Classification Search .............. 324/228, 324/238, 240, 219; 600/109, 112–113
See application file for complete search history.

(56) References Cited

U.S. PATENT DOCUMENTS

| | | | |
|---|---|---|---|
| 3,279,460 A | 10/1966 | Sheldon | |
| 4,340,302 A | 7/1982 | Oku et al. | |
| 4,640,124 A | 2/1987 | Diener et al. | |
| 5,045,936 A | 9/1991 | Lobb et al. | |
| 5,184,601 A | 2/1993 | Putman | |
| 5,217,003 A | 6/1993 | Wilk | |
| 5,670,879 A * | 9/1997 | Zombo et al. ................ | 324/227 |
| 5,738,676 A | 4/1998 | Hammer et al. | |
| 5,808,665 A | 9/1998 | Green | |
| 5,877,819 A | 3/1999 | Branson | |
| 6,011,617 A | 1/2000 | Naudet et al. | |
| 6,031,566 A * | 2/2000 | Leo .................................... | 348/82 |
| 6,332,865 B1 | 12/2001 | Borody et al. | |
| 6,432,046 B1 | 8/2002 | Yarush et al. | |
| 6,542,230 B1 | 4/2003 | Luke et al. | |
| 6,670,808 B2 | 12/2003 | Nath et al. | |
| 6,697,764 B2 | 2/2004 | Corby, Jr. et al. | |
| 7,154,378 B1 | 12/2006 | Ertas et al. | |
| 2002/0042620 A1 | 4/2002 | Julian et al. | |
| 2005/0128288 A1 | 6/2005 | Bernstein et al. | |
| 2007/0225931 A1 | 9/2007 | Morse et al. | |
| 2007/0226258 A1 | 9/2007 | Lambdin et al. | |
| 2008/0242986 A1 | 10/2008 | Ichikawa | |
| 2009/0043516 A1 * | 2/2009 | Liu et al. ........................ | 702/35 |

FOREIGN PATENT DOCUMENTS

WO    WO 2008046209 A1 *    4/2008

OTHER PUBLICATIONS

European Search Report, Application No. 09172494.8, Applicant, GE Inspection Technologies, LP, Mailed, May 11, 2011, 8 pages.

* cited by examiner

*Primary Examiner* — Bot Ledynh (74) *Attorney, Agent, or Firm* — GE Global Patent Operation; Mark A. Conklin (57) ABSTRACT

An inspection apparatus is provided that can include at least one probe receiving unit. The at least one probe receiving unit can be capable of processing data corresponding to one or more of image information of the type that can be generated by a visual inspection probe, eddy current information of the type that can be generated by a eddy current probe, and ultrasound information of the type that can be generated by a ultrasound probe.

15 Claims, 5 Drawing Sheets

INSPECTION APPARATUS FOR PERFORMING INSPECTIONS

BACKGROUND OF THE INVENTION

The present invention relates generally to inspections and specifically to inspection apparatuses for performance of inspections.

Inspection apparatuses are available in multiple varieties. For example, visual inspection apparatuses are used to collect image information respecting an area to be inspected. Visual inspection apparatuses can include an image sensor and imaging optics for focusing an image of a target onto the image sensor.

Eddy current inspection apparatuses can be used to develop information characterizing a target. Eddy current inspection apparatuses generally include an eddy current driver and an eddy current sensor. An eddy current driver induces an eddy current in a target subject to detection and an eddy current sensor senses the induced current. Eddy current inspection apparatuses can be used to detect characteristics of a target. One common use of an eddy current inspection apparatus is to detect defects, such as cracks in a target subject to detection.

Ultrasound inspection apparatuses are available in multiple varieties, and can be used, e.g., in corrosion monitoring in targets subject to inspection. In one form, an ultrasound inspection apparatus can include an oscillator for generation of ultrasonic waves.

Each of the above types of inspection apparatuses can include an elongated inspection tube for insertion through narrow passageways.

Each of the above types of inspection apparatuses can be used for inspection of an industrial equipment article.

However, skilled artisans have noted that a number of characteristics that can be determined using a single inspection apparatus available in the prior art tends to be limited. Often, e.g., an area of an equipment article subject to using a first inspection apparatus needs to be subject to re-inspection using a second inspection apparatus.

SUMMARY OF THE INVENTION

An inspection apparatus is provided that can include at least one probe receiving unit. The at least one probe receiving unit can be capable of processing data corresponding to one or more of image information of the type that can be generated by a visual inspection probe, eddy current information of the type that can be generated by a eddy current probe, and ultrasound information of the type that can be generated by a ultrasound probe.

DETAILED DESCRIPTION OF THE INVENTION

There is provided in one embodiment a probe receiving unit which can receive at least one probe of the following probe types: a visual inspection probe, an eddy current probe, and an ultrasound probe. Incorporated in the visual inspection probe can be components typically associated with a visual inspection apparatus. Incorporated in the eddy current probe can be components typically associated with an eddy current inspection apparatus. Incorporated in the ultrasound probe can be components typically associated with an ultrasound inspection apparatus. Accordingly, an inspection apparatus as described herein in one embodiment can be used to conduct visual inspections, eddy current sensor based inspections, and ultrasound inspections.

Figure 1:
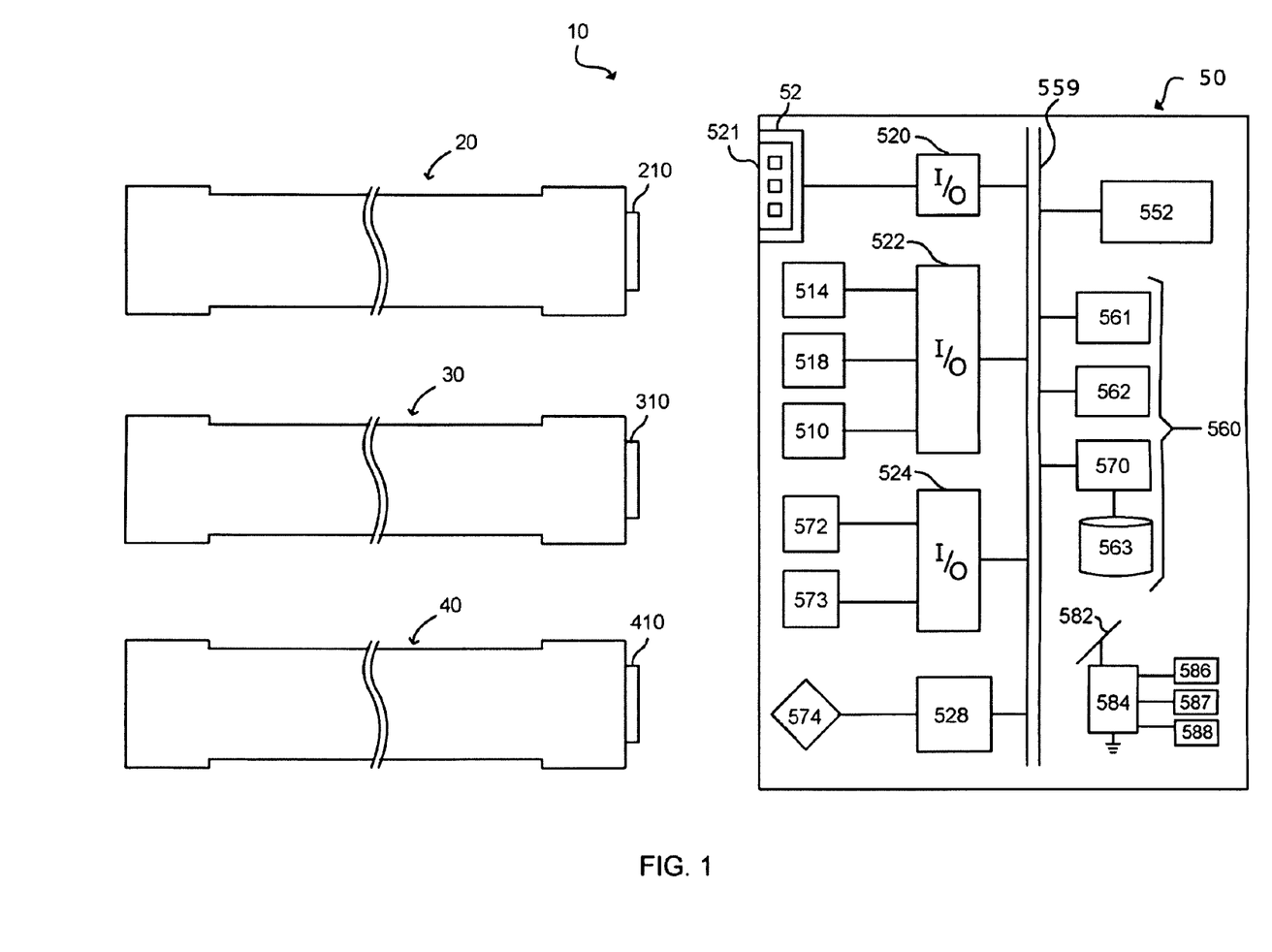
FIG. 1 is an exemplary schematic block diagram illustrating an inspection apparatus in one embodiment of the invention.

An exemplary inspection apparatus 10 is shown in FIG. 1. In the embodiment of FIG. 1, apparatus 10 can include a first probe provided by visual inspection probe 20, a second probe provided by an eddy current probe 30, and a third probe provided by ultrasound probe 40, and probe receiving unit 50. Probe receiving unit 50 can include a probe holder 52 for receiving a probe. Probe receiving unit 50 can be adapted to receive one of first probe 20, second probe 30, and third probe 40 via probe holder 52 at a given time. In one embodiment, probe receiving unit 50 can detachably receive a probe of a variable (e.g., visual, eddy current, ultrasound) probe type. It is understood that an embodiment including probes of any combination of zero, one, two, or three of the above listed probe types are within the scope and the spirit of the invention.

Figure 2:
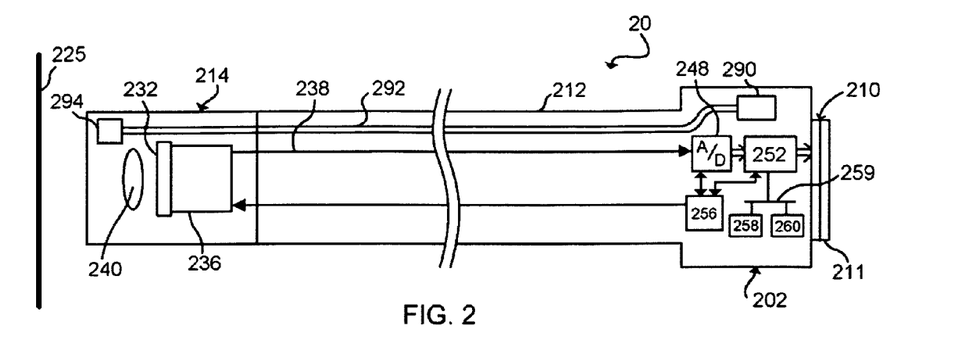
FIG. 2 is a schematic block diagram of a visual inspection probe in an exemplary embodiment.

Referring to aspects of an exemplary visual inspection probe 20 in one embodiment of the invention, components of an exemplary visual inspection probe 20 are shown and described in FIG. 2. Visual inspection probe 20 can include a proximal end 202 an elongated inspection tube 212 and a camera head assembly 214 disposed at a distal end of the elongated inspection tube 212. Elongated inspection tube 212 can be flexible. Camera head assembly 214 can include solid state image sensor 232 and imaging optics 240 comprising one or more lenses. Imaging optics 240 can focus an image of a target 225 onto an active surface of solid state image sensor 232. Solid state image sensor 232 can be, e.g., a CCD or CMOS image sensor. Solid state image sensor 232 can include a plurality of pixels formed in a plurality of rows and columns. Solid state image sensor 232 can be provided on an integrated circuit. Image sensor 232 can generate image signals in the form of analog voltages representative of light incident on each pixel of the image sensor 232. Referring to further aspects of camera head assembly 214, image signal conditioning circuit 236 can be controlled to clock out image signals from image sensor 232. Analog voltages representative of light incident on the various pixels of image sensor 232 can be propagated through image signal conditioning circuit 236 along a cable 238, e.g., a coaxial cable disposed within elongated inspection tube 212. Camera head assembly 214 can include image signal conditioning circuit 236 which conditions analog image signals for input to cable 238 and receives timing and control signals for control of image sensor 232.

Various circuits disposed at a position spaced apart from camera head assembly 214 can receive and process image information generated by image sensor 232. In the exemplary embodiment of FIG. 2, an analog-to-digital converter 248, can receive analog image signals, digitize such signals and transmit digitized image signals to processing circuit 252. In the embodiment shown, processing circuit 252 can be adapted to perform such processing tasks as color matrix processing, gamma processing, and can process digital image signals into a standardized video format, wherein video signals are expressed in a standardized data format. By way of example, video signals output by processing circuit 252 can be in an ITU-R BT656 (4:2:2 YCrCb) video format. Processing circuit 252 can be in communication with a nonvolatile memory 258 and a random access memory 260 through system bus 259. Referring to further components of visual inspection probe 20, probe 20 can include timing generator circuit 256 which can send timing and control signals to image signal conditioning circuit 236 for input to image sensor 232 as well as to analog to digital converter (ADC) 248 and processing circuit 252. Timing generator circuit 256 can send control signals such as exposure timing signals and frame rate timing signals to image signal conditioning circuit 236 for input to image sensor 232. In one embodiment, ADC 248, processing circuit 252, and timing generator circuit 256 can be provided on separate integrated circuits (ICs). In one embodiment, ADC 248, processing circuit 252, and timing generator circuit 256 are provided as part of commercially available chipset, e.g., the 814612 chipset available from SONY.

In another aspect of visual inspection probe 20, probe 20 can include a light source 290 (e.g., an arc lamp or a bank of LEDs), which can be disposed at a position spaced apart from camera head assembly 214. Probe 20 can also include an illumination fiber optic bundle 292 receiving light emitted from the light source. Fiber optic bundle 292 can be disposed in elongated inspection tube 212 so that fiber optic bundle 292 can relay light emitted from light source 290 through elongated inspection tube 212 and to camera head assembly 214. A distal end of fiber optic bundle 292 can be interfaced to diffuser 294 for diffusing illumination light. Fiber optic bundle 292 and diffuser 294 can be arranged to project light over an area approximately corresponding to a field of view of image sensor 232.

A probe in accordance with probe 20 can generate image information in the form of image signals. With a probe in accordance with probe 20 received in probe receiving unit 50, CPU 552 can process image data corresponding to the image information.

In a further aspect, a probe in accordance with visual inspection probe 20 can include a power supply (not shown) for powering components of probe 20. Such a power supply can be connected to power and ground contacts of connector 211, and can be powered by power supply 584 of probe receiving unit 50 when probe 20 is received on probe receiving unit 50.

Figure 3:
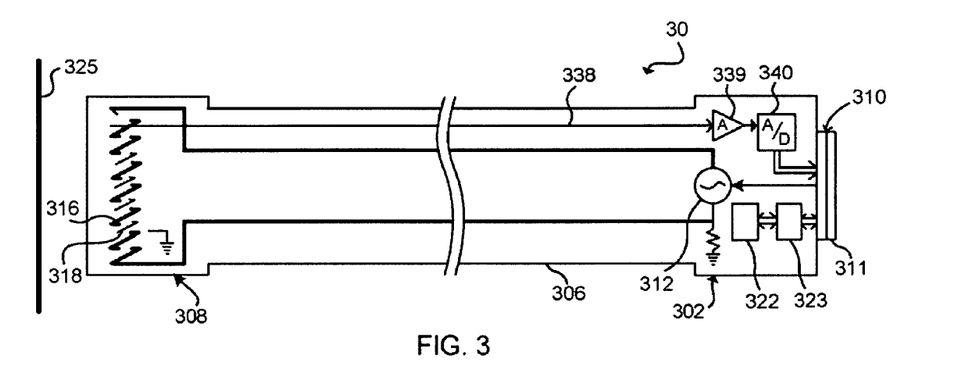
FIG. 3 is a schematic block diagram of an eddy current probe in an exemplary embodiment.

Referring now to eddy current probe 30, eddy current probe 30 can be provided in a variety of forms. In an eddy current probe 30, a time varying drive signal can excite eddy currents in the test piece via a suitable probe (coil). The eddy currents are detected either by sensing the current in the exciting coil or by a secondary magnetic field sensing device, such as a coil, GMR or Hall Effect sensor.

The sensed signal can be conditioned. This usually involves amplification, some level of pre-filtering and in some cases where high defect detectivity is required, subtraction of a reference or balance signal. The signal is processed to extract its real and imaginary components using a suitable analog or digital circuit. The real and imaginary components of the sensed signal can be displayed, in a complex impedance plane, as a function of time or as a function of position.

Eddy current probe 30, in the specific exemplary embodiment of FIG. 3 can be implemented as a reflection probe with two coils, and can include a current driver 312, a driver coil 316, and a pickup coil 318. Probe 30 can include a proximal end 302, an elongated inspection tube 306, and a head assembly 308. Elongated inspection tube 306 can be rigid or flexible. Driver coil 316 and pickup coil 318 can be disposed in head assembly 308. When current driver 312 is activated, a current can flow through driver coil 316 to induce a current in a target 325 (e.g., a metal surface being subject to inspection). Pickup coil 318, which can be regarded as an eddy current sensor, can sense the induced current in the target and can output a voltage signal (an eddy current signal) varying in accordance with the induced current. In the probe of FIG. 3, the output voltage signal output by pickup coil 318 can be transmitted along cable 338 and can be amplified by amplifier 339 and input into ADC 340 which converts the voltage into a digital value which is output to a multi-pin connector which can be included in interface 310 for connection to probe receiving unit 50. The signal output by pickup coil 318 can also be subject to pre-filtering and in some embodiments, subtraction of a reference or balance signal. For long probes, additional amplifiers can be disposed more proximate pickup coil 318. The output voltage output by pickup coil 318 can be expected to vary as probe 30 is moved from location to location. The output signal voltage can be processed to determine characteristics of a target being subject to inspection. For example, when probe 30 is moved into proximity with a metal surface containing a crack, the output voltage signal generated by pickup coil 318 can be in such form as to be processable to detect the presence of a crack, e.g., by comparison with a signal generated by probe 30, when probe 30 is not in proximity with the crack. Shown as being provided as a reflection probe, eddy current probe 30 can also be implemented as an absolute probe, a differential probe, a reflection probe, an unshielded probe, and a shielded probe. Digital signals that are presented to probe receiving unit 50 for further processing can include a representation of the signal picked up by pickup coil 318. (In the case of a differential probe, two such signals will be presented to probe receiving unit 50.) The digital signal can be processed in accordance with a plurality of different applications, e.g., a surface crack detection application, a fastener inspection application, a weld inspection application, a corrosion detection application.

A probe in accordance with probe 30 can generate eddy current information in the form of eddy current signals. With a probe in accordance with probe 30 received in probe receiving unit 50, CPU 552 can process eddy current data corresponding to the eddy current information.

In a further aspect, a probe in accordance with eddy current inspection probe 30 can include a power supply (not shown)

for powering components of probe 30. Such a power supply can be connected to power and ground contacts of connector 311, and can be powered by power supply 584 of probe receiving unit 50 when probe 30 is received on probe receiving unit 50.

Figure 4:
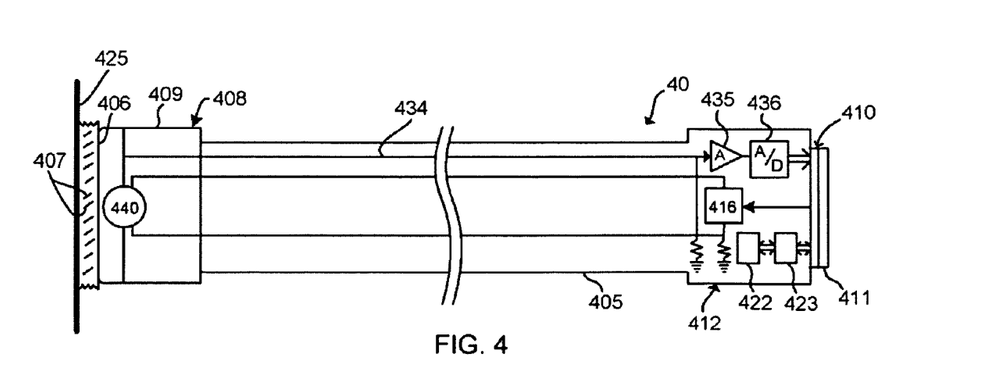
FIG. 4 is a schematic block diagram of an ultrasound probe in an exemplary embodiment.

An ultrasound probe in an exemplary embodiment is shown and described in FIG. 4. Ultrasound probe 40 can comprise head assembly 408, elongated inspection tube 405 and proximal end 412. Elongated inspection tube 405 can be flexible. Oscillator 440 for emitting ultrasonic waves can be disposed in head assembly 408 of probe 40. Probe 40 can be adapted so that ultrasonic waves emitted by oscillator 440 vary in response to voltages supplied by drive circuit 416 which is communicatively coupled to circuitry of probe receiving unit 50 when probe 40 is attached to probe receiving unit 50. Oscillator 440 can be provided by a piezoelectric element, of, e.g., crystal, ceramic, or polymer construction. Referring to further aspects of ultrasound probe 40, coupling media 407 for allowing propagation of acoustic waves can be disposed intermediate of target 425 and head assembly 408. Examples of such coupling media are de-gassed water, coupling media for ultrasonic testing, oil based coupling media for ultrasonic testing, cream based coupling media for ultrasonic testing, and gel based coupling media for ultrasonic testing. Coupling media 407 can be in loose form or else can be of shape-retaining construction or stored in a flexible acoustically transmissive container. Coupling media 407 in one embodiment can be disposed in head assembly 408. A housing 409 for head assembly 408 can comprise flexible material e.g., silicon rubber to allow head assembly 408 to be placed in good contact with a target 425 via a suitable coupling media being subject to ultrasonic testing, (e.g., a metal surface). Ultrasonic waves generated by oscillator 440 can be reflected from target 425 after propagating through coupling media 407, and can thereafter be propagated through coupling media 407 and picked up by transducer 406. Transducer 406 can be regarded as an ultrasound sensor. Transducer 406 in turn, can generate ultrasonic signals representative of the reflected ultrasonic waves. The generated ultrasonic signals can be transmitted along cable 434, and can be input into amplifier 435 for amplification and the input for conversion into digital form into ADC 436, which can output multi-bit digital signals to connector 411, which is adapted for connection to probe receiving unit 50. For longer probes, additional amplifiers can be disposed in closer proximity to transducer 406. For developing data indicating characteristics of a target, ultrasonic waves emitted by oscillator 440 can be transmitted in the form of a pulse. Data received by probe receiving unit 50 for processing can include representations of an initial pulse and echoes from the structure under test, including recorded times of emitted ultrasonic waves, and recorded times for return echoes, from which digital information respecting a structure under test can be determined.

A probe in accordance with ultrasound probe 40 can generate ultrasound information in the form of ultrasound signals. With a probe in accordance with ultrasound probe 40 engaged with probe receiving unit 50, CPU 552 of probe receiving unit 50 can produce ultrasound data corresponding to the ultrasound information.

In a further aspect, a probe in accordance with ultrasound inspection probe 40 can include a power supply (not shown) for powering components of probe 40. Such a power supply can be connected to power and ground contacts of connector 411, and can be powered by power supply 584 of probe receiving unit 50 when probe 40 is received on probe receiving unit 50.

In one embodiment, each of visual inspection probe 20, eddy current probe 30, and ultrasound probe 40 can be dedicated probes. That is, visual inspection probe 20 can be restricted from generating either eddy current information or ultrasound information. Eddy current probe 30 can be restricted from generating either image information or ultrasound information and ultrasound probe 40 can be restricted from generating either image information of eddy current information.

Referring to further aspects of apparatus 10, apparatus 10 can include probe receiving unit 50. Probe receiving unit 50 can incorporate a central processing unit (CPU) 552. The CPU 552 can be implemented, e.g., as a general purpose microprocessor integrated circuit or a specialized microprocessor integrated circuit such as a digital signal processor. Probe receiving unit 50 can also incorporate a memory 560 which can include a system memory and a storage memory. A system memory of probe receiving unit 50 can include a random access memory (RAM) 561 and a nonvolatile memory 562 shown as being provided by an EPROM. A storage memory of probe receiving unit 50 can be provided by storage device 563, e.g., a hard drive. Storage device 563 can be communicatively coupled to the system bus 559, e.g., via a storage device controller 570. The circuits making up memory 560 can be in communication with CPU 552 via a system bus 559. Application programs can be stored in memory 560.

In other aspects of probe receiving unit 50, probe receiving unit 50 in one embodiment can include a keyboard 514 for initiation of control signals by an operator and a display 510 for displaying information. Keyboard 514 and display 510 can be regarded as making up a user interface. A user interface of probe receiving unit 50 can also include a joystick 518. Apparatus 10 can be adapted so that when joystick 518 is actuated, control signals for causing articulation of an elongated inspection tube of a probe attached to probe receiving unit 50 are initiated. The keyboard, display, and joystick can be communicatively coupled to the system bus 559, e.g., via an input/output (I/O) controller 522.

Probe receiving unit 50 can also include a serial I/O interface 572 and a parallel I/O interface 573. Serial I/O interface 572, can be, e.g., an Ethernet, a USB or other interface enabling communication between apparatus 10 and an external computer. Parallel I/O interface 573 can be, e.g., a compact flash interface. Serial I/O interface 572 and parallel I/O interface 573 can be communicatively coupled to the system bus 559, e.g., via an input/output (I/O) controller 524.

The various circuit components of probe receiving unit 50 can be mounted on a printed circuit board assembly 582, which can be powered by power supply 584. Power supply 584 can be powered by a plurality of alternative power sources including rechargeable battery 586, serial interface (e.g., USB) supply 587, and AC/DC transformer 588.

Probe receiving unit 50 can also include an RF communication interface, e.g., an IEEE 802.11x family wireless transceiver interface. An RF communication interface can comprise RF transceiver 574 and RF communication controller 528. RF communication controller 528 can be communicatively coupled to the system bus 559.

Apparatus 10 can incorporate a TCP/IP networking communication protocol stack and can be incorporated in a local area network or a wide area network including a plurality of computers, where one or more of the computers also incorporate a TCP/IP networking communication protocol stack.

In one aspect, probe receiving unit 50 can include at least one resource of the following resource types: visual probe resources, eddy current probe resources, and ultrasound probe resources. Apparatus 10 can be adapted so that CPU 552 of probe receiving unit 50 can be communicatively coupled with a probe of a variable probe type that is detachably received in probe receiving unit 50. Apparatus 10 can be adapted so that the resources of each resource type are active when a probe of a corresponding probe type is received in the probe receiving unit 50 via holder 52, i.e., visual probe resources are active when the visual inspection probe 20 is received in the probe receiving unit 50 via holder 52, the eddy current probe resources are active when the eddy current probe 30 is received in the probe receiving unit 50 via holder 52, and ultrasound probe resources are active when the ultrasound probe 40 is received in the probe receiving unit 50 via holder 52. The visual probe resources can include program code adapting CPU 552 to process image information of the type received by CPU 552 when visual inspection probe 20 is received on holder 52. The eddy current probe resources can include program code adapting CPU 552 to process eddy current information of the type received by CPU 552 when eddy current probe 30 is received on holder 52. The ultrasound probe resources can include program code adapting CPU 552 to process ultrasound data corresponding to ultrasound information generated by an ultrasound probe, the data being of the type received by CPU 552 when a probe in accordance with ultrasound probe 40 is received on holder 52 so that it is received in probe receiving unit 50.

In one embodiment, resources (i.e., the visual probe resources, eddy current probe resources, ultrasound probe resources) corresponding to one or more of probe types 20, 30, and 40 can be stored in a nonvolatile memory 258, 322, 422 of the respective probes 20, 30, and 40 and inspection apparatus 10 can be adapted so that when a probe 20, 30, or 40 is attached to probe holder 52 the resources stored in the nonvolatile memory of the particular probe are automatically transmitted from the probe 20, 30 or 40 to probe receiving unit 50 for storage into a nonvolatile memory 562 of probe receiving unit 50 and for execution by CPU 552. Once stored in probe receiving unit 50, resources of a particular probe do not require retransmission each time the particular probe is re-engaged with probe holder 52.

In another aspect, probe receiving unit 50 can be adapted to automatically detect the probe type of a probe attached to holder 52 and can be further adapted to automatically activate the resources of the corresponding resource type depending on the type of the probe attached. Probe receiving unit 50 can include a watch program monitoring input data received by CPU 552. The input data can be expected to have different probe type signature characteristics depending on which of first probe 20, second probe 30 or third probe 40 is attached. For example, image information can be characterized by the presence of the image header containing, e.g., the image format, type of encoding, image size, etc. Eddy current information can be characterized by the presence in every input word of a bit pattern containing, e.g., the ADC conversion rate. Ultrasound probe information can be characterized by the presence in every input word of a bit pattern containing, e.g., the ADC conversion rate. CPU 552 can be adapted to process data input thereto in order to determine the probe type of the probe attached to holder 52.

In another embodiment, probe receiving unit 50 can automatically detect the type of probe attached to holder 52. Each of the probes 20, 30, and 40 can be adapted to store a probe type identifying information in a nonvolatile memory. A probe type identifying information can be, e.g., a binary string, or an alphanumeric string, including an alphanumeric string containing a manufacturer's part number, e.g., a serial number. The serial number can be a unique serial number or a non-unique serial number. Where CPU 552 is in communication with a lookup table correlating serial number to probe type, CPU 552 can determine a probe type utilizing a serial number by reading the serial number and referencing the serial number probe type lookup table. A nonvolatile memory can be, e.g., an erasable programmable read-only memory (EPROM). Each of the probes 20, 30, and 40 can be adapted to send a message including message data containing the probe type identifying information responsively to receiving a probe type query over a respective interface 210, 310, and 410.

In the exemplary visual probe of FIG. 2, nonvolatile memory 258 can be coupled to interface 210 via system bus 259 and processing circuit 252. In the exemplary eddy current probe 30 of FIG. 3, the nonvolatile memory 322 can be coupled to interface 310 via memory selection circuit 323. In the exemplary ultrasound probe of FIG. 4, nonvolatile memory 422 is communicatively coupled to interface 410 via memory selection circuit 423.

In one embodiment, each of the interfaces 210, 310, and 410 can be implemented as a bidirectional data transfer interface, e.g., an I2C bus interface by Philips Semiconductors. In accordance with the embodiment including an I2C interface, the CPU 552 can act as a bus master and send a general call message advertising its own bus address to all the devices connected to the bus. In accordance with the I2C specification, each of the devices connected to the bus must acknowledge the general call message. In one embodiment, following the acknowledgement by a probe 20, 30 or 40 currently received in the probe receiving unit 50, the CPU 552 can switch to the receiving mode and each of the probes currently received in the probe receiving unit 50 can transmit a message containing the probe type identifying information.

In a variant of the embodiment including an I2C interface, the CPU 552 can have a pre-defined I2C bus address. A probe 20, 30 or 40, upon engaging with the probe receiving unit 50, can acquire the bus address and transmit a message containing the probe type identifying information to the CPU 552 using its pre-defined I2C bus address.

In another embodiment, each of the probes can have a pre-defined address, and the probe type identifying information can be derived by the CPU 552 from the probe bus address, e.g., if the bus address ranges are pre-assigned to specific probe types. Specifically, in one embodiment, probe receiving unit 50 can be in communication with a lookup table correlating pre-assigned bus addresses to probe types. CPU 552 can determine a probe type utilizing a bus address by reading the bus address and referencing the bus address probe type lookup table, to receive the probe type of an attached probe.

When activating the visual probe resources, the eddy current probe resources or the ultrasound probe resources, the apparatus 10 can, e.g., perform digital signal processing of the signal received from the corresponding probe, including, e.g., image scaling, zoom, enhancement, etc. for the signal received from a visual inspection probe, and, e.g., voltage signal frequency filtering for the signals received from an eddy current probe or ultrasound probe.

Referring to aspects of holder 52, holder 52 can include a connector 521. Connector 521 can be implemented as a standardized IEEE 4888 multi-pin electrical connector. Connector 521 can be provided either by a male connector or a female connector. Where connector 521 is provided by a female connector, interfaces 210, 310, and 410 of probes 20, 30, and 40 can include respective connectors 211, 311, 411 provided by male connectors. Where connector 521 is provided by a male connector, interfaces 210, 310, and 410 of probes 20, 30, and 40 respectively can include connectors provided by female connectors. Connector 521 can be communicatively coupled to system bus 559, e.g., via I/O controller 520.

Exemplary functioning of CPU 552 when visual inspection probe 20 is attached in one embodiment is now described. When visual inspection probe 20 is attached to (received by) holder 52, visual probe resources can be made active so that CPU 552 can receive the formatted video output from processing circuit 252 for further processing. Visual probe resources can include program code executable by CPU 552. With visual probe resources active, CPU 552 can be adapted to perform a variety of processing tasks such as frame averaging, scaling, zoom, overlaying, merging, image capture, flipping, image enhancement and distortion correction. When visual inspection probe 20 is attached to holder 52 to activate visual probe resources, CPU 552 can successively output frames of image data captured by processing circuit 252 to display 510. A successively output set of frames or image data can be referred to as an output streaming video. With visual probe resources active, among other functions, CPU 552 can generate a control signal to take a picture in response, e.g., to a button of keyboard 514 being actuated. CPU 552, in one embodiment, can be provided by a TMS320DM642 video imaging DSP of the type available from Texas Instruments.

Exemplary functional aspects of CPU 552 when a probe in the form of eddy current probe 30 is attached to holder 52 are now described. When an eddy current probe 30 is attached to holder 52, eddy current probe resources are activated in one embodiment so that CPU 552 can process input eddy current information to determine various information e.g., whether a crack is present in a target. Eddy current probe resources can include program code executable by CPU 552. The processing of data with eddy current probe resources active can include signal filtering to filter out signal components caused, e.g., by the interference noise from the instrumentation, by varying distance to an edge of the sample being scanned, etc.

When a crack is detected to be present, the CPU 552 with ultrasound probe resources active can cause an indicator to be presented to an operator indicating the presence of a crack. For example, CPU 552 can cause displaying the following text: "CRACK DETECTED!" on display 510 when CPU 552 has determined by processing of input eddy current information that a crack is present. Eddy current probe resources activated when a probe in accordance with eddy current probe 30 is attached can include resources to adapt CPU 552 to extract real and imaginary components from data corresponding to an eddy current signal generated by probe 30 and to display on display 510, in a complex impedance plane, the real and imaginary components.

Exemplary functional aspects of CPU 552 when a probe in the form of an ultrasound probe 40 is attached to holder 52 are now described when a probe in accordance with ultrasound probe 40 is attached to holder 52, ultrasound probe resources can be activated so that CPU 552 determines a depth of an object utilizing a recorded time of an emitted ultrasonic wave and a recorded time of a return pulse as sensed at various points over an area transducer 406. When an ultrasound probe 40 is attached to holder 52, ultrasound probe resources can be activated in one embodiment so that CPU 552 can process input ultrasound probe information to measure the wall thickness of a target, or to determine whether a crack is present in a target. Ultrasound probe resources can include program code executable by CPU 552. The processing can include signal filtering to filter out signal components caused, e.g., by the interference noise from the instrumentation. The processing can further include detecting frequency changes in the reflected sound which are indicative of a crack in the target being tested.

Visual probe resources, eddy current probe resources, and ultrasound probe resources can include user interface resources that are activated so that activation of a user interface component of probe receiving unit 50, such as keyboard 514 or joystick 518 results in a particular effect depending on a probe type of a probe presently received in probe receiving holder 52.

For example, when a probe in accordance with a visual probe type is attached to activate visual probe resources, user interface resources can be activated in such manner that actuation of a user interface component by a user can result in e.g., a video recording being made, a still picture being captured.

User interface resources that can be activated when a probe in accordance with visual inspection probe 20 attached can also include resources allowing a user to input parameters for use in making distance calculations. In one embodiment, a visual inspection probe 20 can be adapted to project a reference feature (e.g., a shadow) onto a target. With probe 20 attached, visual inspection resources can be actuated to enable a user using keyboard 514 and/or joystick 518 to locate cursors on a displayed image representation of the target displayed on display 510 to indicate an area designated for distance calculation. User interface resources can also be activated so that a user using keyboard 514 can initiate a measurement calculation. When a measurement calculation is initiated, CPU 552 running under the control of image processing resources activated by the attachment of probe 20 can process the image representation including a representation of the projected reference feature to output a distance measurement based on the location of the reference feature and the user located cursors on the representation.

Eddy current probe resources activated when a probe in accordance with eddy current probe 30 is attached can also enable control signals for controlling probe 30 to be initiated using probe receiving unit 50. Eddy current probe resources can adapt probe receiving unit 50 so that using the user interface of probe receiving unit 50, an operator can change characteristics (amplitude, frequency) of current output by current driver 312.

With an ultrasound probe 40 attached to activate ultrasound probe resources, activation of a user interface component of probe receiving unit 50 can result in control of a component e.g., oscillator 440 of ultrasound probe 40.

Thus, apparatus 10 can be adapted so that changing of a probe held in holder 52 to a probe of a different probe type, readapts (reconfigures) a function of a user interface component e.g., a keyboard 514 or display 510 from a first configuration for control of a component of a probe in accordance with a first probe type to a second function for control of a component of a probe in accordance with a second probe type.

Figure 5:
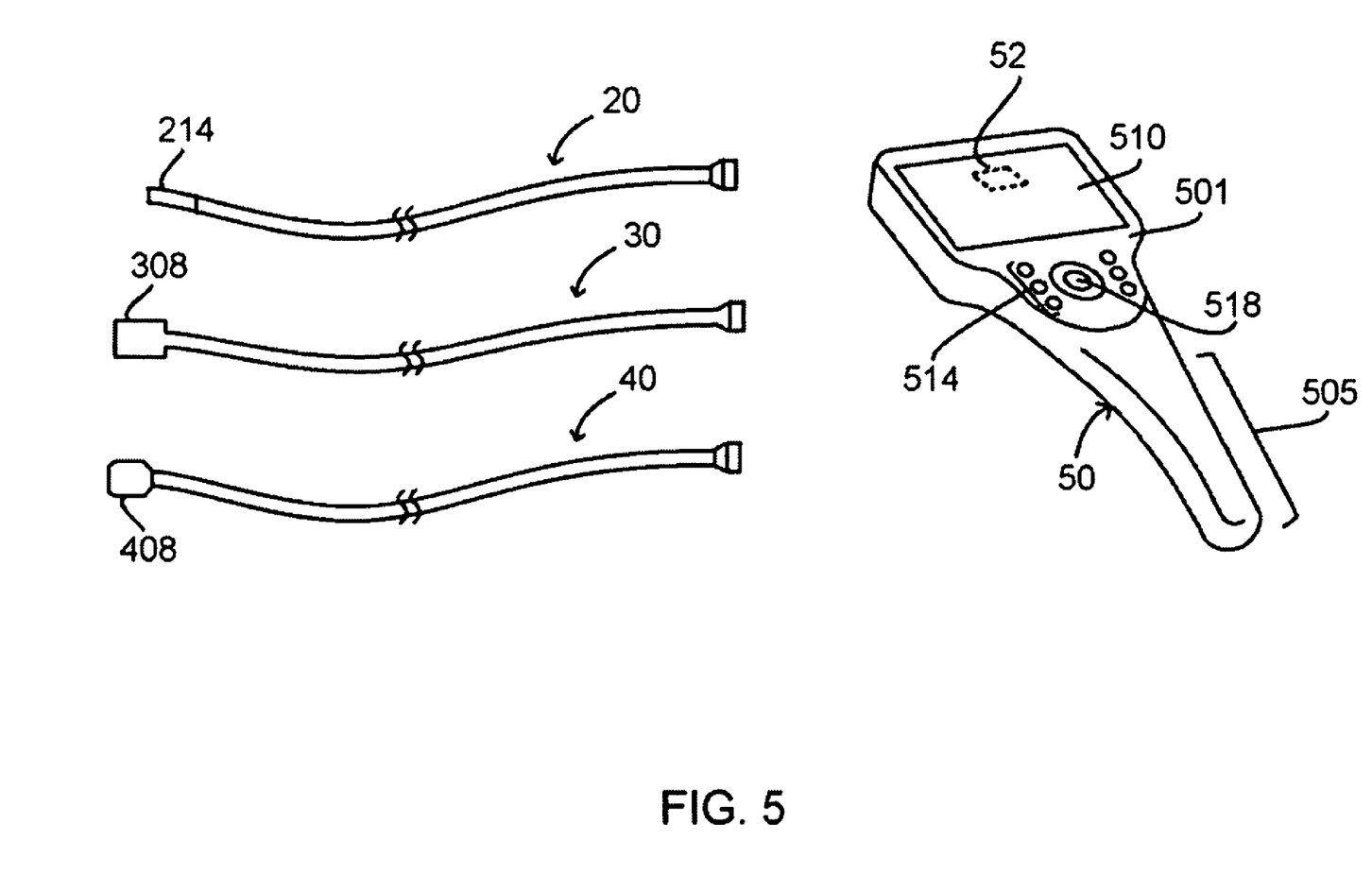
FIG. 5 is an exemplary physical form view of an inspection apparatus having first, second, and third alternative probes, each of the probes being in accordance with a different probe type.

Referring to FIG. 5, a physical view of apparatus 10 in one embodiment is shown and described. In the embodiment shown, probe receiving unit 50 includes housing 501. Housing 501 in the embodiment of FIG. 5 is a portable housing shaped and sized to be hand held. Housing 501 in the embodiment of FIG. 5 commonly has disposed thereon probe holder 52, keyboard 514, joystick 518, and display 510. In the embodiment shown probe receiving unit 50 includes a handle 505. In one embodiment, apparatus 10 includes a single portable housing having components as described with reference to element 50 of FIG. 1 and holder 52 is disposed on the single housing. In another embodiment, probe receiving unit 50 includes more than one housing and the components described with reference to element 50 of FIG. 1 are distributed among the more than one housing. In such an embodiment having plural housings, all of the housings can be portable and hand held or only one of the plurality of housings can be portable and hand held. In an embodiment wherein probe receiving unit 50 comprises plural housings, probe receiving holder 52 (or holders 52a and 52b as described herein) can be disposed on one of the plural housings (such as a stationary housing or a portable hand held housing of the plural housings). In one embodiment, probe receiving unit 50 is provided by a desk top personal computer (PC), in which holder 52 is disposed on a main PC housing and display 510 and keyboard 514 are tethered to the housing. When a probe such as a probe in accordance with probe 20, 30, or 40 is held by a holder 52, 52a, or 52b to define a hand held probe, a proximal end of the probe can be held in a certain position relative to the housing on which the holder is disposed.

Figure 6:
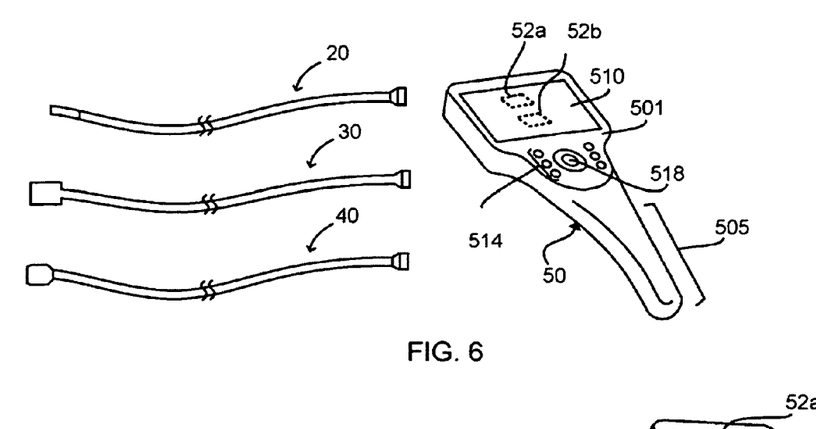
FIG. 6 is a physical form view of an embodiment of an inspection apparatus having a plurality of probe holders.
Figure 7:
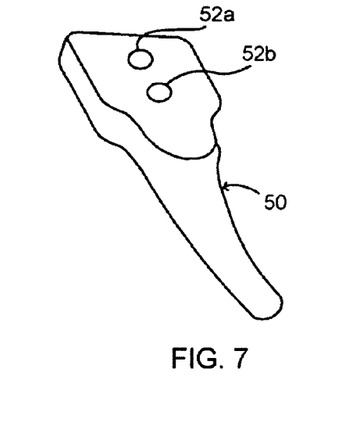
FIG. 7 is a perspective view of a probe receiving unit in one embodiment, having a plurality of probe holders.

In another embodiment illustrated in FIGS. 6 (front view) and 7 (rear view), probe receiving unit 50 can have at least two probe holders 52a-52b. Probe receiving unit 50 can be adapted to receive a probe in accordance with visual inspection probe 20 via probe holder 52a, and one of a second visual inspection probe 20, a probe in accordance with eddy current probe 30, or a probe in accordance with ultrasound probe 40 via probe holder 52b at a given time. Probe receiving unit 50 in one embodiment can be adapted so that probe holder 52 detachably receives a probe in accordance with probe 20. In another embodiment, probe receiving unit 50 can be adapted so that probe holder 52a non-detachably receives a probe in accordance with probe 20. Probe receiving unit 50 can be adapted so that probe holder 52b detachably receives a probe in accordance with probe 20, 30, 40. Probe receiving unit 50 can be adapted so that probe holder 52b non-detachably receives a probe in accordance with probe 20, 30, 40. The embodiment with at least two probe holders, one of which is adapted to receive a visual inspection probe, allows the operator of the inspection apparatus to control more accurately the movement of the second visual inspection probe 20, eddy current probe 30, or ultrasound probe 40 along the surface being tested, by receiving constant visual feedback from visual inspection probe 20. Inspection apparatus 10 image data e.g., in the form of streaming video images corresponding to image information being generated by probe 20 received in holder 52a can be displayed on display 510 of probe receiving unit 50.

Figure 8:
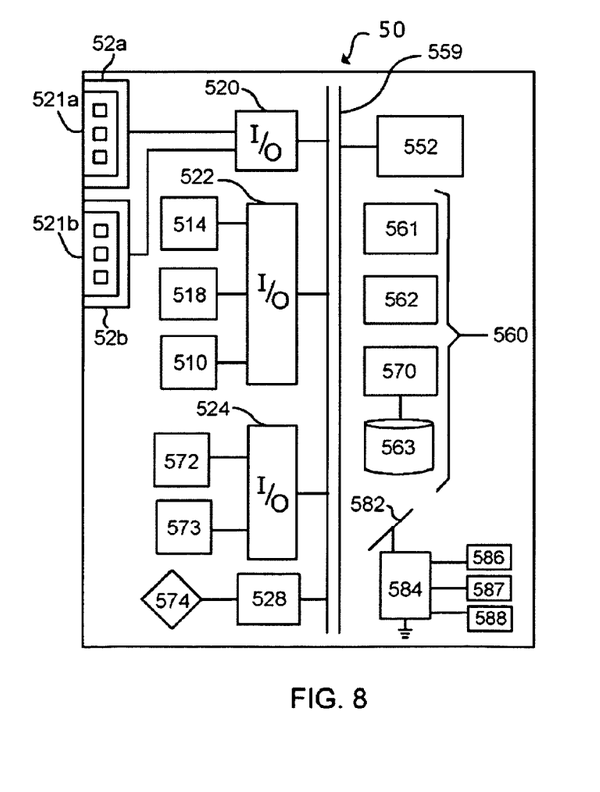
FIG. 8 is a schematic block diagram of a probe receiving unit having a plurality of probe holders.

FIG. 8 illustrates an exemplary block diagram of probe receiving unit 50 including two probe holders 52a and 52b. Probe holders 52a and 52b can include connectors 521a and 521b, respectively. Connectors 521a-521b can be implemented as a standardized IEEE 4888 multi-pin electrical connector. Connectors 521a-521b can be provided either by a male connector or a female connector. Connectors 521a-521b can be communicatively coupled to system bus 559, e.g., via I/O controller 520.

Figure 9:
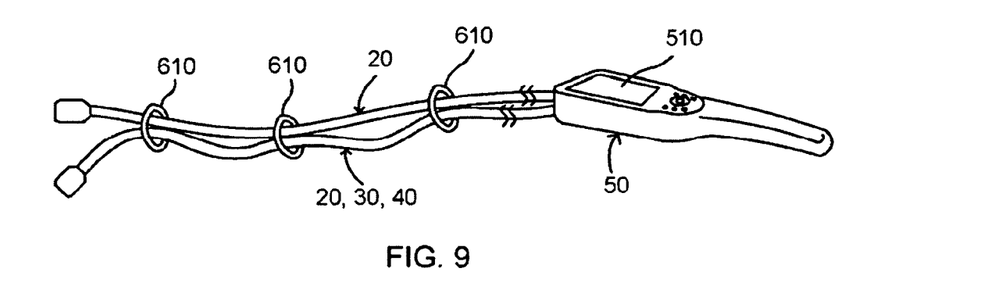
FIG. 9 is a perspective view of an embodiment of an inspection apparatus having a plurality of probes, and being adapted (configured) so that the plurality of probes are mechanically coupled.
Figure 10:
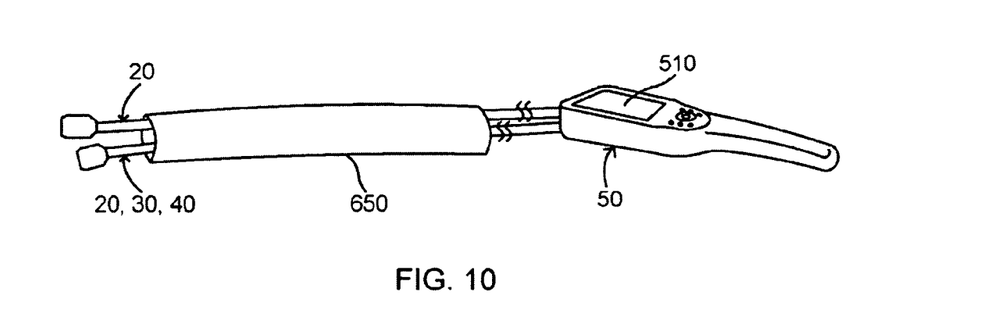
FIG. 10 is a perspective view of another embodiment of an inspection apparatus having a plurality of probes and being adapted so that the plurality of probes are mechanically coupled.

In an embodiment having a plurality of probe holders, e.g., probe holders 52a and 52b, apparatus 10 can include multiple probe type resources as described previously herein, i.e., visual inspection probe resources, eddy current probe resources, and ultrasound probe resources, that are selectively activated in response to a probe type corresponding to the resources being received on probe receiving unit 50. Probe receiving unit 50 in such an embodiment can have a multi-tasking operating system so that CPU 552 can contemporaneously process data corresponding to information generated by a first probe or a first probe type (e.g., visual inspection probe 20) while processing data corresponding to information generated by a probe of a same or different probe type. So that the guiding provided by the visual inspection probe received by first probe holder 52a is enhanced, apparatus 10 can be adapted so that first and second probes currently received on probe receiving unit 50 are mechanically coupled. Apparatus 10 in one embodiment can include a coupling apparatus for mechanically coupling a pair of probes respectively relating to first probe holder 52a and second probe holder 52b. In the embodiment of FIG. 9, a coupling mechanism is provided by a plurality of clamping devices 610 coupling a pair of probes at various locations along the respective length thereof, which may be, e.g., resilient rings, clips, clasps, clamps, or the like. In the embodiment of FIG. 10, a coupling apparatus is provided by an elongated tube 650 disposed about respective lengths of elongated inspection tubes of first and second probes.

Figure 11:
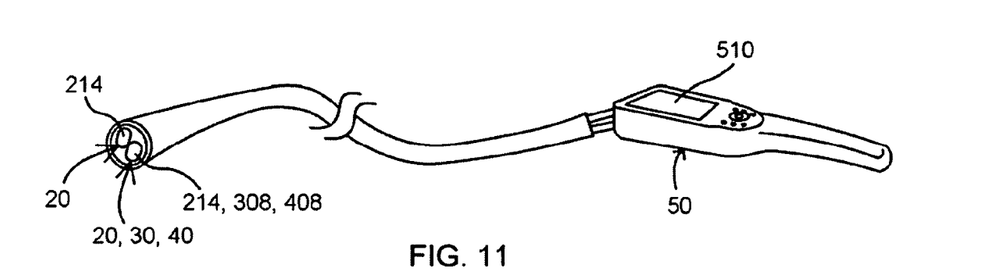
FIG. 11 is a perspective view of another embodiment of an inspection apparatus having a plurality of probes and being adapted so that the plurality of probes are mechanically coupled.

In the embodiment of FIG. 11, elongated tube 650 extends substantially the entire length of a pair of first and second probes, and extends to encompass both the head assembly 214 of visual inspection probe 20 and the head assembly 214, 308 or 408 of the second probe. In the embodiment of FIG. 11, the head assembly of two probes and elongated tube 650 terminate at substantially the same distance from probe receiving unit 50.

A small sample of systems methods and apparatus that are described herein is as follows:

A1. An inspection apparatus for performing inspections, said inspection apparatus comprising:
 (a) a probe receiving unit;
 (b) a central processing unit (CPU) incorporated in said probe receiving unit;
 (c) a probe holder adapted to receive a probe, said probe holder disposed on said probe receiving unit and being communicatively coupled to said CPU;
 (d) wherein said CPU is capable of processing data corresponding to two or more of: image information of the type that can be generated by a visual inspection probe, eddy current information of the type that can be generated by an eddy current probe, and ultrasound information of the type that can be generated by an ultrasound probe; and
 (e) wherein said probe receiving unit is adapted so that resources for adapting said CPU for processing data corresponding to one of image information, eddy current information, and ultrasound information can be activated responsively to a probe being received on said probe receiving unit via said probe holder.

A2. The inspection apparatus of claim A1, wherein said inspection apparatus includes a first probe selected from the group consisting of a visual inspection probe type, an eddy current probe type, and an ultrasound probe type.

A3. The inspection apparatus of claim A1, wherein said inspection apparatus includes a first probe being of a probe type selected from the group consisting of a visual inspection probe type, an eddy current probe type, and an ultrasound probe type, and wherein said inspection apparatus includes a second probe being of a probe type different from the probe type of said first probe and being of a probe type selected from the group consisting of a visual inspection probe type, an eddy current probe type, and an ultrasound probe type.

A4. The inspection apparatus of claim A1, wherein said probe receiving unit is adapted to detachably receive a probe via said probe holder.

B1. An inspection apparatus for performing inspections, said inspection apparatus comprising:

(a) a probe receiving unit;

(b) a central processing unit (CPU) incorporated in said probe receiving unit;

(c) a probe holder disposed on said probe receiving unit communicatively coupled to said CPU;

(d) a first probe having an elongated inspection tube and being of a certain probe type;

(e) a second probe having an elongated inspection tube and being of a probe type different from said certain probe type;

(f) wherein each of said certain probe type and said probe type different from said certain probe type are probe types selected from the group consisting of a visual inspection probe type having an elongated inspection tube and an image sensor for generating image signals, an eddy current probe type having an elongated inspection tube and an eddy current sensor and an ultrasound probe type having an elongated inspection tube and an ultrasound sensor;

(g) wherein said inspection apparatus is adapted so that said probe receiving unit can detachably receive, via said probe holder, one of said first probe and said second probe at a given time; and (h) wherein said CPU is adapted to process data corresponding to information generated by a probe presently received in said probe holder, whether said first probe or said second probe is presently received in said probe holder.

B2. The inspection apparatus of claim B1, wherein said probe receiving unit includes a hand held housing, and wherein said CPU is disposed in said hand held housing, and wherein said inspection apparatus is adapted so that when said first probe or said second probe is held in said probe holder to define a held probe, a proximal end of said held probe is held in a certain position relative to said hand held housing.

B3. The inspection apparatus of claim B1, wherein said inspection apparatus includes at least two of: visual probe resources adapting said inspection apparatus for processing image data, eddy current probe resources adapting said inspection apparatus for processing eddy current data, and ultrasound probe resources adapting said inspection apparatus for processing ultrasound data.

B4. The inspection apparatus of claim B1, wherein said inspection apparatus includes at least two of: visual probe resources adapting said inspection apparatus for processing image data, eddy current probe resources adapting said inspection apparatus for processing eddy current data and ultrasound probe resources adapting said inspection for processing of ultrasound data wherein said inspection apparatus is adapted so that said inspection apparatus can detect a probe type of a probe presently being held in said probe holder, and is further adapted so that said inspection apparatus activates an appropriate one of said visual probe resources, said eddy current probe resources, and said ultrasound probe resources responsively to a detection of said probe type.

B5. The inspection apparatus of claim B1, wherein said inspection apparatus includes at least two of: visual probe resources adapting said inspection apparatus for processing image data, eddy current probe resources adapting said inspection apparatus for processing eddy current data, and ultrasound probe resources adapting said inspection apparatus for processing ultrasound data;

wherein said inspection apparatus is adapted so that said CPU receives probe data from a probe received in said probe holder whether said probe is said first probe or said second probe;

wherein said inspection apparatus is further adapted to run a software program which monitors said probe data to detect probe type signature characteristics so that said inspection apparatus can detect a probe type of a probe presently received in said probe holder, said probe type signature characteristics identifying a probe type of a probe presently received in said probe holder;

wherein said inspection apparatus is further adapted so that said inspection apparatus activates an appropriate one of said visual probe resources, said eddy current probe resources, and said ultrasound probe resources responsively to a detection of said probe type.

B6. The inspection apparatus of claim B1, wherein said inspection apparatus includes at least two of: visual probe resources adapting said inspection apparatus for processing image data, eddy current probe resources adapting said inspection apparatus for processing eddy current data, and ultrasound probe resources adapting said inspection apparatus for processing ultrasound data;

wherein said each of said first probe and said second probe includes a nonvolatile memory storing probe type identifying information;

wherein said CPU is adapted to communicatively couple with said first probe responsively to said first probe engaging with said probe receiving unit, and wherein said CPU is adapted to communicatively couple with said second probe responsively to said second probe engaging with said probe receiving unit;

wherein said CPU is further adapted to receive message data including said probe type identifying information of said first probe when said first probe is received in said probe receiving unit;

wherein said CPU is further adapted to receive message data including said probe type identifying information of said second probe when said second probe is received in said probe receiving unit;

so that said inspection apparatus can detect a probe type of a probe presently received in said probe receiving unit and activate an appropriate one of said visual probe resources, said eddy current probe resources, and said ultrasound probe resources responsively to said detection of said probe type.

B7. The inspection apparatus of claim B6, wherein said message data received from said first probe when said first probe is received in said probe receiving unit includes data from the group consisting of binary string data, alphanumeric string data, part number data, and serial number data.

B8. The inspection apparatus of claim B1, wherein said first probe includes a bidirectional data transfer interface, and wherein said CPU is adapted to communicatively couple via said bidirectional data transfer interface with said first probe when said probe receiving unit receives said first probe.

B9. The inspection apparatus of claim B1, wherein said inspection apparatus includes at least two of: visual probe resources adapting said inspection apparatus for processing image data, eddy current probe resources adapting said inspection apparatus for processing eddy current data, and ultrasound probe resources adapting said inspection apparatus for processing ultrasound data;

wherein said each of said first probe and said second probe includes a nonvolatile memory storing probe type identifying information;

wherein said CPU is adapted to communicatively couple with said first probe responsively to said first probe engaging with said probe receiving unit, and wherein said CPU is adapted to communicatively couple with said second probe responsively to said second probe engaging with said probe receiving unit;

wherein said CPU is further adapted to receive one of a binary string or an alphanumeric string including said probe type identifying information of said first probe when said first probe is received in said probe receiving unit;

wherein said CPU is further adapted to receive one of a binary string or an alphanumeric string including said probe type identifying information of said second probe when said second probe is received in said probe receiving unit;

so that said inspection apparatus can detect a probe type of a probe presently received in said probe receiving unit and can activate an appropriate one of said visual probe resources, said eddy current probe resources, and said ultrasound probe resources responsively to said detection of said probe type.

B10. The inspection apparatus of claim B1, wherein said inspection apparatus includes at least two of: visual probe resources adapting said inspection apparatus for processing image data, eddy current probe resources adapting said inspection apparatus for processing eddy current data and ultrasound probe resources adapting said inspection apparatus for processing ultrasound data;

wherein said each of said first probe and said second probe includes a nonvolatile memory storing probe type identifying information, said probe type identifying information being in the form of an address pre-assigned to each of said first probe and said second probe, each of said first probe and said second probe having a bidirectional data transfer interface;

wherein said CPU is adapted to communicatively couple via said bidirectional data transfer interface of said first probe with said first probe responsively to said first probe engaging with said probe receiving unit, and wherein said CPU is adapted to communicatively couple via said bidirectional data transfer interface of said second probe with said second probe responsively to said second probe engaging with said probe receiving unit;

wherein said CPU is further adapted to receive over said bidirectional data transfer interface of said first probe said pre-assigned address of said first probe when said first probe is received in said probe receiving unit;

wherein said CPU is further adapted to receive over said bi-directional data transfer interface of said second probe said pre-assigned address of said second probe when said second probe is received in said probe receiving unit;

wherein said CPU is further adapted to detect a probe type utilizing a received pre-assigned address received from either of said first probe or said second probe, whichever is presently received by said probe receiving unit;

so that said inspection apparatus can detect a probe type of a probe presently received in said probe receiving unit and can activate an appropriate one of said visual probe resources, said eddy current probe resources, and said ultrasound probe resources responsively to said detection of said probe type.

B11. The inspection apparatus of claim B1, wherein said inspection apparatus includes each of: visual probe resources adapting said inspection apparatus for processing image data, eddy current probe resources adapting said inspection apparatus for processing eddy current data, and ultrasound probe resources adapting said inspection apparatus for processing ultrasound data;

wherein said each of said first probe and said second probe includes a nonvolatile memory storing probe type identifying information, said probe type identifying information being in the form of a serial number pre-assigned to each of said first probe and said second probe;

wherein said CPU is adapted to communicatively couple with said first probe responsively to said first probe engaging with said probe receiving unit, and wherein said CPU is adapted to communicatively couple with said second probe responsively to said second probe engaging with said probe receiving unit;

wherein said CPU is further adapted to receive said pre-assigned serial number of said first probe when said first probe is received in said probe receiving unit;

wherein said CPU is further adapted to receive said pre-assigned serial number of said second probe when said second probe is received in said probe receiving unit;

wherein said CPU is further adapted to detect a probe type utilizing a received pre-assigned serial number received from either of said first probe or said second probe, whichever is presently received by said probe receiving unit;

so that said inspection apparatus can detect a probe type of a probe presently received in said probe receiving unit and can activate an appropriate one of said visual probe resources, said eddy current probe resources, and said ultrasound probe resources responsively to said detection of said probe type.

B12. The inspection apparatus of claim B1, wherein said inspection apparatus includes at least two of: visual probe resources adapting said inspection apparatus for processing image data, eddy current probe resources adapting said inspection apparatus for processing eddy current data, and ultrasound probe resources adapting said inspection apparatus for processing ultrasound data;

wherein said each of said first probe and said second probe includes a nonvolatile memory storing probe type identifying information;

wherein said CPU is adapted to communicatively couple via a bidirectional data transfer interface of said first probe with said first probe responsively to said first probe engaging with said probe receiving unit, and wherein said CPU is adapted to communicatively couple via said bidirectional data transfer interface of said second probe responsively to said second probe engaging with said probe receiving unit;

wherein said CPU is further adapted to receive over said bidirectional data transfer interface of said first probe message data including said probe type identifying information of said first probe when said first probe is received in said probe receiving unit;

wherein said CPU is further adapted to receive over said bidirectional data transfer interface of said second probe message data of said second probe including said probe type identifying information of said second probe when said second probe is received in said probe receiving unit;

wherein said CPU is further adapted so that said CPU sends a general call message over one of said bidirectional data transfer interfaces of said first probe or said second probe responsively to one of said first probe or said second probe being received in said probe receiving unit to which said message data from said first probe or said second probe is responsively received;

so that said inspection apparatus can detect a probe type of a probe presently received in said probe receiving unit and activate an appropriate one of said visual probe resources, said eddy current probe resources, and said ultrasound probe resources responsively to said detection of said probe type.

B13. The inspection apparatus of claim B1, wherein said inspection apparatus further includes a third probe, said third probe being of a probe type different from a probe type of each of said first probe and said second probe, said third probe also being of a probe type selected from the group consisting of a visual probe, an eddy current probe, and an ultrasound probe, wherein said inspection apparatus comprises visual probe resources adapting said inspection apparatus for processing image data, eddy current probe resources adapting said inspection apparatus for processing eddy current data, and ultrasound probe resources adapting said inspection apparatus for processing ultrasound data, and wherein said inspection apparatus is further adapted so that said probe receiving unit can detachably receive via said probe holder said third probe.

B14. The inspection apparatus of claim B1, wherein said inspection apparatus further includes first resources associated with said first probe selected from the group consisting of visual probe resources, eddy current probe resources and ultrasound probe resources, said first resources including program code stored in a nonvolatile memory of said first probe that is transmitted for running on said probe receiving unit responsively to said first probe being received in said probe holder.

B15. The inspection apparatus of claim B1, wherein said probe receiving unit has disposed thereon a keyboard and a display.

B16. The inspection apparatus of claim B1, wherein said probe receiving unit has a housing and wherein said probe receiving unit has disposed on said housing a keyboard and a display.

B17. The inspection apparatus of claim B1, wherein said probe receiving unit has a hand held housing and wherein said probe receiving unit has disposed on said hand held housing a keyboard and a display.

B18. The inspection apparatus of claim B1, wherein said probe receiving unit has a housing that commonly has disposed thereon a keyboard, display and said probe holder.

B19. The inspection apparatus of claim B1, wherein said inspection apparatus is adapted so that said probe receiving unit further comprises a user interface component, and is further adapted so that a function of said user interface component is reconfigured when a state of said inspection apparatus changes between a first state in which said first probe is held in said probe holder and a second state in which said second probe is held in said probe holder.

C1. An inspection apparatus for performing inspections, said inspection apparatus comprising:
 (a) a probe receiving unit having a housing;
 (b) a central processing unit (CPU) incorporated in said probe receiving unit;
 (c) a first probe holder disposed on said probe receiving unit and being communicatively coupled to said CPU;
 (d) a second probe holder also disposed on said probe receiving unit and being communicatively coupled to said CPU;
 (e) a display disposed on said probe receiving unit;
 (f) a keyboard disposed on said probe receiving unit;
 (g) a first probe being a visual inspection probe including an elongated inspection tube and an image sensor for generating image signals, said inspection apparatus being adapted so that said probe receiving unit can receive via said first probe holder said first probe;
 (h) a second probe including an elongated inspection tube, wherein a probe type of said second probe is selected from the group consisting of a visual inspection probe type having an elongated inspection tube and an image sensor, an eddy current probe type having an elongated inspection tube and an eddy current sensor, and an ultrasound probe type having an elongated inspection tube and an ultrasound sensor, said inspection apparatus being adapted so that said probe receiving unit can receive via said second probe holder said second probe;
 (i) wherein said probe receiving unit is adapted so that said CPU can process image data corresponding to image signals of the type that can be generated by said image sensor, and is further adapted so that said CPU can process data corresponding to information generated by said second probe.

C2. The inspection apparatus of claim C1, wherein said inspection apparatus is adapted so that when said first probe and said second probe are held by said probe receiving unit, a proximal end of said each of said first probe and second probe is held in a certain position relative to said probe receiving unit.

C3. The inspection apparatus of claim C1, wherein said CPU runs a multitasking operating system adapting said CPU so that said CPU can process data corresponding to information generated by said first probe contemporaneously while processing data corresponding to information generated by said second probe.

C4. The inspection apparatus of claim C1, wherein said inspection apparatus further comprises a coupling apparatus that mechanically couples said first probe and said second probe so that respective elongated inspection tubes of said first probe and said second probe are held in contact with one another or in close proximity with one another.

C5. The inspection apparatus of claim C1, wherein said inspection apparatus further comprises a coupling apparatus that mechanically couples said first probe and said second probe so that respective elongated inspection tubes of said first probe and said second probe are held in contact with one another or in close proximity with one another, said coupling apparatus comprising at least one clamping device.

C6. The inspection apparatus of claim C1, wherein said inspection apparatus further comprises a coupling apparatus that mechanically couples said first probe and said second probe so that respective elongated inspection tubes of said first probe and said second probe are held in contact with one another or in close proximity with one another, said coupling apparatus comprising an elongated tube.

C7. The inspection apparatus of claim C1, wherein said inspection apparatus further comprises an apparatus that mechanically couples said first probe and said second probe so that respective elongated inspection tubes of said first probe and said second probe are held in contact with one another or in close proximity with one another, the apparatus comprising a plurality of clamping devices disposed at spaced apart locations along respective lengths of elongated inspection tubes of said first and second probes.

C8. The inspection apparatus of claim C1, wherein said at least one of said keyboard and said display are commonly disposed on a common hand held housing that further has disposed thereon said first probe holder and said second probe holder.

C9. The inspection apparatus of claim C1, wherein said first probe holder is adapted to detachably receive said first probe.

C10. The inspection apparatus of claim C1, wherein said second probe holder is adapted to detachably receive said second probe.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. An inspection apparatus comprising:
   (a) a probe receiving unit;
   (b) a central processing unit (CPU) incorporated in said probe receiving unit,
   (c) a probe holder disposed on said probe receiving unit communicatively coupled to said CPU;
   (d) a first probe having an elongated inspection tube and being of a certain probe type;
   (e) a second probe having an elongated inspection tube and being of a probe type different from said certain probe type;
   (f) wherein each of said certain probe type and said probe type different from said certain probe type are probe types selected from the group consisting of a visual inspection probe type having an elongated inspection tube and an image sensor for generating image signals, an eddy current probe type having an elongated inspection tube and an eddy current sensor and an ultrasound probe type having an elongated inspection tube and an ultrasound sensor;
   (g) wherein said inspection apparatus is adapted so that said probe receiving unit can detachably receive, via said probe holder, one of said first probe and said second probe at a given time;
   (h) wherein said CPU is adapted to process data corresponding to information generated by a probe presently received in said probe holder, whether said first probe or said second probe is presently received in said probe holder;
   (i) wherein said inspection apparatus includes at least two of: visual probe resources adapting said inspection apparatus for processing image data, eddy current probe resources adapting said inspection apparatus for processing eddy current data, and ultrasound probe resources adapting said inspection apparatus for processing ultrasound data;
   (j) wherein said inspection apparatus is adapted so that said CPU receives probe data from a probe received in said probe holder whether said probe is said first probe or said second probe;
   (k) wherein said inspection apparatus is further adapted to run a software program which monitors said probe data to detect probe type signature characteristics so that said inspection apparatus can detect a probe type of a probe presently received in said probe holder, said probe type signature characteristics identifying a probe type of a probe presently received in said probe holder; and
   (l) wherein said inspection apparatus is further adapted so that said inspection apparatus activates an appropriate one of said visual probe resources, said eddy current probe resources, and said ultrasound probe resources responsively to a detection of said probe type.

2. The inspection apparatus of claim 1, wherein said probe receiving unit includes a hand held housing, wherein said CPU is disposed in said hand held housing, and wherein said inspection apparatus is adapted so that when said first probe or said second probe is held in said probe holder to define a held probe, a proximal end of said held probe is held in a certain position relative to said hand held housing.

3. The inspection apparatus of claim 1, wherein said inspection apparatus includes at least two of visual probe resources adapting said inspection apparatus for processing image data, eddy current probe resources adapting said inspection apparatus for processing eddy current data, and ultrasound probe resources adapting said inspection apparatus for processing ultrasound data; wherein said each of said first probe and said second probe includes a nonvolatile memory storing probe type identifying information;
   wherein said CPU is adapted to communicatively couple with said first probe responsively to said first probe engaging with said probe receiving unit, and wherein said CPU is adapted to communicatively couple with said second probe responsively to said second probe engaging with said probe receiving unit;
   wherein said CPU is further adapted to receive message data including said probe type identifying information of said first probe when said first probe is received in said probe receiving unit;
   wherein said CPU is further adapted to receive message data including said probe type identifying information of said second probe when said second probe is received in said probe receiving unit;
   so that said inspection apparatus can detect a probe type of a probe presently received in said probe receiving unit and activate an appropriate one of said visual probe resources, said eddy current probe resources, and said ultrasound probe resources responsively to said detection of said probe type.

4. The inspection apparatus of claim 1, wherein said inspection apparatus further includes first resources associated with said first probe selected from the group consisting of visual probe resources, eddy current probe resources and ultrasound probe resources, said first resources including program code stored in a nonvolatile memory of said first probe that is transmitted for running on said probe receiving unit responsively to said first probe being received in said probe holder.

5. The inspection apparatus of claim 1, wherein said probe receiving unit has a hand held housing and wherein said probe receiving unit has disposed on said hand held housing a keyboard and a display.

6. The inspection apparatus of claim 1, wherein said probe receiving unit has a housing that commonly has disposed thereon a keyboard, display and said probe holder.

7. The inspection apparatus of claim 1, wherein said inspection apparatus is adapted so that said probe receiving unit further comprises a user interface component, and is further adapted so that a function of said user interface component is reconfigured when a state of said inspection apparatus changes between a first state in which said first probe is held in said probe holder and a second state in which said second probe is held in said probe holder.

8. An inspection apparatus for performing inspections, said inspection apparatus comprising:
   (a) a probe receiving unit having a housing;
   (b) a central processing unit (CPU) incorporated in said probe receiving unit;
   (c) a first probe holder disposed on said probe receiving unit and being communicatively coupled to said CPU;
   (d) a second probe holder also disposed on said probe receiving unit and being communicatively coupled to said CPU;
   (e) a display disposed on said probe receiving unit;
   (f) a keyboard disposed on said probe receiving unit;
   (g) a first probe being a visual inspection probe including an elongated inspection tube and an image sensor for generating image signals, said inspection apparatus being adapted so that said probe receiving unit can receive is said first probe holder said first probe;
   (h) a second probe including an elongated inspection tube, wherein a probe type of said second probe is selected from the group consisting of a visual inspection probe type having an elongated inspection tube and an image sensor, an eddy current probe type having an elongated inspection tube and an eddy current sensor, and an ultrasound probe type having an elongated inspection tube and an ultrasound sensor, said inspection apparatus being adapted so that said probe receiving unit can receive via said second probe holder said second probe (i) wherein said probe receiving unit is adapted so that said CPU can process image data corresponding to image signals of the type that can be generated by said image sensor, and is further adapted so that said CPU can process data corresponding to information generated h said second probe; and (j) wherein said inspection apparatus further comprises an apparatus that mechanically couples said first probe and said second probe so that respective elongated inspection tubes of said first probe and said second probe are held in contact with one another or in close proximity with one another, the apparatus comprising a plurality of clamping devices disposed at spaced apart locations along respective lengths of elongated inspection tubes of said first and second probes.

9. The inspection apparatus of claim 8, wherein said inspection apparatus is adapted so that when said first probe and said second probe are held by said probe receiving unit, a proximal end of said each of said first probe and second probe is held in a certain position relative to said probe receiving unit.

10. The inspection apparatus of claim 8, wherein said CPU runs a multitasking operating system adapting said CPU so that said CPU can process data corresponding to information generated by said first probe contemporaneously while processing data corresponding to information generated by said second probe.

11. The inspection apparatus of claim 8, wherein said at least one of said keyboard and said display are commonly disposed on a common hand held housing that further has disposed thereon said first probe holder and said second probe holder.

12. The inspection apparatus of claim 1, wherein said inspection apparatus further comprises a coupling apparatus that mechanically couples said first probe and said second probe so that respective elongated inspection tubes of said first probe and said second probe are held in contact with one another or in close proximity with one another.

13. The inspection apparatus of claim 1 wherein said inspection apparatus further comprises a coupling apparatus that mechanically couples said first probe and said second probe so that respective elongated inspection tubes of said first probe and said second probe are held in contact with one another or in close proximity with one another, said coupling apparatus comprising an elongated tube.

14. The inspection apparatus of claim 1, wherein said inspection apparatus further comprises an apparatus that mechanically couples said first probe and said second probe so that respective elongated inspection tubes of said first probe and said second probe are held in contact with one another or in close proximity with one another, the apparatus comprising a plurality of clamping devices disposed at spaced apart locations along respective lengths of elongated inspection tubes of said first and second probes.

15. The inspection apparatus of claim 8, wherein said inspection apparatus includes at least two of:

visual probe resources adapting said inspection apparatus for processing image data, eddy current probe resources adapting said inspection apparatus for processing eddy current data, and ultrasound probe resources adapting said inspection apparatus for processing ultrasound data;

wherein said inspection apparatus is adapted so that said CPU receives probe data from a probe received in said probe holder whether said probe is said first probe or said second probe;

wherein said inspection apparatus is further adapted to run a software program which monitors said probe data to detect probe type signature characteristics so that said inspection apparatus can detect a probe type of a probe presently received in said probe holder, said probe type signature characteristics identifying a probe type of a probe presently received in said probe holder; and wherein said inspection apparatus is further adapted so that said inspection apparatus activates an appropriate one of said visual probe resources, said eddy current probe resources, and said ultrasound probe resources responsively to a detection of said probe type.

\* \* \* \* \*

UNITED STATES PATENT AND TRADEMARK OFFICE
CERTIFICATE OF CORRECTION

PATENT NO.         : 8,217,646 B2
APPLICATION NO.    : 12/253548
DATED              : July 10, 2012
INVENTOR(S)        : Karpen It is certified that error appears in the above-identified patent and that said Letters Patent is hereby corrected as shown below:

In the Claims:

In Column 19, Line 5, in Claim 1, delete "unit," and insert -- unit; --, therefor.

In Column 19, Line 10, in Claim 1, delete "haying" and insert -- having --, therefor.

In Column 19, Line 62, in Claim 3, delete "two of visual" and insert -- two of: visual --, therefor.

In Column 20, Line 64, in Claim 8, delete "receive is" and insert -- receive via --, therefor.

In Column 21, Line 7, in Claim 8, delete "holder said second probe" and insert -- holder said second probe; --, therefor.

In Column 21, Line 12, in Claim 8, delete "generated h" and insert -- generated by --, therefor.

In Column 22, Line 3, in Claim 13, delete "1" and insert -- 1, --, therefor.

Signed and Sealed this
Sixth Day of November, 2012

David J. Kappos
*Director of the United States Patent and Trademark Office*